(12) United States Patent
Marshall

(10) Patent No.: US 7,702,492 B2
(45) Date of Patent: Apr. 20, 2010

(54) SYSTEM AND METHOD FOR GENERATING AN ELECTRONIC MODEL FOR A DENTAL IMPRESSION HAVING A COMMON COORDINATE SYSTEM

(75) Inventor: Michael Craig Marshall, Savage, MN (US)

(73) Assignee: GeoDigm Corporation, Chanhassen, MN (US)

( * ) Notice: Subject to any disclaimer, the term of this patent is extended or adjusted under 35 U.S.C. 154(b) by 671 days.

(21) Appl. No.: 10/799,344

(22) Filed: Mar. 11, 2004

(65) Prior Publication Data

US 2005/0203726 A1 Sep. 15, 2005

(51) Int. Cl.
G06G 7/48 (2006.01)
A61C 19/04 (2006.01)

(52) U.S. Cl. ............................................. 703/6; 433/68

(58) Field of Classification Search ..................... 703/6, 703/11; 433/41, 67, 68
See application file for complete search history.

(56) References Cited

U.S. PATENT DOCUMENTS

| | | | |
|---|---|---|---|
| 3,084,438 A | 4/1963 | Goodfriend | |
| 4,123,768 A | 10/1978 | Kilshaw et al. | |
| 4,123,786 A | 10/1978 | Cramer | |
| 4,182,312 A | 1/1980 | Mushabac | |
| 4,402,326 A | 9/1983 | Okano et al. | |
| 4,436,684 A | 3/1984 | White | |
| 4,575,805 A | 3/1986 | Moermann et al. | |
| 4,611,288 A | 9/1986 | Duret et al. | |
| 4,673,352 A | 6/1987 | Hansen | |
| 4,742,464 A | 5/1988 | Duret et al. | |
| 4,752,964 A | 6/1988 | Okada et al. | |
| 4,775,946 A | 10/1988 | Anjyo | |
| 4,799,785 A | 1/1989 | Keates et al. | |
| 4,837,732 A | 6/1989 | Brandestini et al. | |
| 4,862,371 A | 8/1989 | Maekawa | |
| 4,862,391 A | 8/1989 | Ohhashi | |
| 4,935,635 A | 6/1990 | O'Harra | |
| 4,983,120 A | 1/1991 | Coleman et al. | |

(Continued)

FOREIGN PATENT DOCUMENTS

IL 120867 5/1997

(Continued)

OTHER PUBLICATIONS

Alcaniz, M. et al., "An Advanced System for the Simulation and Planning of Orthodontic Treatment," *Medical Image Analysis*, vol. 2, No. 1, pp. 61-77 (Mar. 1998) (1 page abstract).

(Continued)

*Primary Examiner*—Paul L Rodriguez
*Assistant Examiner*—Eunhee Kim
(74) *Attorney, Agent, or Firm*—Merchant & Gould P.C.

(57) ABSTRACT

A system for generating an electronic model having a common coordinate system includes a scanning device; a first plate module; and a second plate module. Each of the plate modules is configured to separately couple to the scanning device. The plate modules also can be moveably coupled together using an articulation device. Each of the plate modules includes alignment structures (e.g., spheres) to facilitate determining a position and orientation of the plate modules within a coordinate system of the scanning device.

6 Claims, 11 Drawing Sheets

U.S. PATENT DOCUMENTS

| | | | |
|---|---|---|---|
| 5,020,993 A | 6/1991 | Levandoski | |
| 5,027,281 A | 6/1991 | Rekow et al. | |
| 5,113,424 A | 5/1992 | Burdea et al. | |
| 5,121,333 A | 6/1992 | Riley et al. | |
| 5,150,457 A | 9/1992 | Behm et al. | |
| 5,184,306 A | 2/1993 | Erdman et al. | |
| 5,198,827 A | 3/1993 | Seaton | |
| 5,198,877 A | 3/1993 | Schulz | |
| 5,224,049 A | 6/1993 | Mushabac | |
| 5,257,184 A | 10/1993 | Mushabac | |
| 5,257,203 A | 10/1993 | Riley et al. | |
| 5,267,293 A | 11/1993 | Virta | |
| 5,273,429 A | 12/1993 | Rekow et al. | |
| 5,320,528 A | 6/1994 | Alpern et al. | |
| 5,338,198 A | 8/1994 | Wu et al. | |
| 5,340,309 A | 8/1994 | Robertson | |
| 5,343,391 A | 8/1994 | Mushabac | |
| 5,347,454 A | 9/1994 | Mushabac | |
| 5,359,511 A | 10/1994 | Schroeder et al. | |
| 5,368,478 A | 11/1994 | Andreiko et al. | |
| 5,372,502 A | 12/1994 | Massen et al. | |
| 5,395,238 A | 3/1995 | Andreiko et al. | |
| 5,416,822 A | 5/1995 | Kunik | |
| 5,431,562 A | 7/1995 | Andreiko et al. | |
| 5,440,393 A | 8/1995 | Wenz | |
| 5,442,572 A | 8/1995 | Kiridena et al. | |
| 5,447,432 A | 9/1995 | Andreiko et al. | |
| 5,448,472 A | 9/1995 | Mushabac | |
| 5,454,068 A | 9/1995 | Ramanujam | |
| 5,454,717 A | 10/1995 | Andreiko et al. | |
| 5,458,487 A | 10/1995 | Komatsu et al. | |
| RE35,169 E | 3/1996 | Lemchen et al. | |
| 5,518,397 A | 5/1996 | Andreiko et al. | |
| 5,533,895 A | 7/1996 | Andreiko et al. | |
| 5,549,476 A | 8/1996 | Stern | |
| 5,562,448 A | 10/1996 | Mushabac | |
| 5,569,578 A | 10/1996 | Mushabac | |
| 5,588,430 A | 12/1996 | Bova et al. | |
| 5,605,459 A | 2/1997 | Kuroda et al. | |
| 5,683,243 A | 11/1997 | Andreiko et al. | |
| 5,730,151 A | 3/1998 | Summer et al. | |
| 5,800,174 A | 9/1998 | Anderson | |
| 5,823,778 A | 10/1998 | Schmitt et al. | |
| 5,842,858 A | 12/1998 | Truppe | |
| 5,879,158 A | 3/1999 | Doyle et al. | |
| 5,880,962 A | 3/1999 | Andersson et al. | |
| 5,882,192 A | 3/1999 | Bergersen | |
| 5,905,658 A | 5/1999 | Baba | |
| 5,977,979 A | 11/1999 | Clough et al. | |
| 5,989,199 A | 11/1999 | Cundari et al. | |
| 6,015,289 A | 1/2000 | Andreiko et al. | |
| 6,068,482 A | 5/2000 | Snow | |
| 6,123,544 A | 9/2000 | Cleary | |
| 6,143,003 A | 11/2000 | Cosman | |
| 6,152,731 A * | 11/2000 | Jordan et al. | 433/73 |
| 6,217,334 B1 * | 4/2001 | Hultgren | 433/215 |
| 6,227,850 B1 | 5/2001 | Chishti et al. | |
| 6,244,861 B1 | 6/2001 | Andreiko et al. | |
| 6,250,918 B1 | 6/2001 | Sachdeva et al. | |
| 6,318,994 B1 | 11/2001 | Chishti et al. | |
| 6,322,359 B1 | 11/2001 | Jordan et al. | |
| 6,322,728 B1 | 11/2001 | Brodkin et al. | |
| 6,334,853 B1 | 1/2002 | Kopelman et al. | |
| 6,364,660 B1 * | 4/2002 | Durbin et al. | 433/29 |
| 6,371,761 B1 | 4/2002 | Cheang et al. | |
| 6,406,292 B1 | 6/2002 | Chishti et al. | |
| 6,409,504 B1 | 6/2002 | Jones et al. | |
| 6,436,684 B1 | 8/2002 | Woodage et al. | |
| 6,450,807 B1 | 9/2002 | Chisti et al. | |
| 6,471,511 B1 | 10/2002 | Chishti et al. | |
| 6,554,613 B1 | 4/2003 | Sachdeva et al. | |
| 6,579,095 B2 | 6/2003 | Marshall et al. | |
| 6,602,070 B2 | 8/2003 | Miller et al. | |
| 6,608,628 B1 | 8/2003 | Ross et al. | |
| 6,632,089 B2 | 10/2003 | Rubbert et al. | |
| 6,648,640 B2 | 11/2003 | Rubbert et al. | |
| 6,688,886 B2 | 2/2004 | Hughes et al. | |
| 6,726,478 B1 | 4/2004 | Isiderio et al. | |
| 6,783,360 B2 | 8/2004 | Chishti | |
| 6,905,337 B1 | 6/2005 | Sachdeva | |
| 6,925,198 B2 | 8/2005 | Scharlack et al. | |
| 7,362,890 B2 | 4/2008 | Scharlack et al. | |
| 2001/0002310 A1 | 5/2001 | Chishti et al. | |
| 2002/0015934 A1 | 2/2002 | Rubbert et al. | |
| 2002/0031743 A1 | 3/2002 | Kim | |
| 2002/0081554 A1 | 6/2002 | Marshall et al. | |
| 2003/0224316 A1 | 12/2003 | Marshall | |
| 2004/0015327 A1 | 1/2004 | Sachdeva et al. | |
| 2004/0023183 A1 | 2/2004 | Miller et al. | |
| 2004/0066877 A1 | 4/2004 | Arai et al. | |
| 2004/0110110 A1 | 6/2004 | Chishti et al. | |
| 2005/0019721 A1 | 1/2005 | Chishti | |
| 2005/0028826 A1 | 2/2005 | Palmisano | |
| 2005/0095562 A1 | 5/2005 | Sporbert et al. | |
| 2005/0153255 A1 | 7/2005 | Sporbert et al. | |
| 2005/0271996 A1 | 12/2005 | Sporbert et al. | |
| 2008/0002869 A1 | 1/2008 | Scharlack et al. | |

FOREIGN PATENT DOCUMENTS

| | | |
|---|---|---|
| IL | 120892 | 5/1997 |
| IL | 121872 | 9/1997 |
| WO | WO 98/32394 A1 | 7/1998 |

OTHER PUBLICATIONS

Alcaniz, M. et al., "A System for the Simulation and Planning of Orthodontic Treatment Using a Low Cost 3D Laser Scanner for Dental Anatomy Capturing," *Studies in Health Technology and Informatics*, vol. 62, pp. 8-14 (1999) (1 page abstract).

Andrews, L., "The six keys to normal occlusion," *American Journal of Orthodontics*, vol. 62, No. 3, cover pages, table of contents, and pp. 296-309 (Sep. 1972).

Baker, H., "Building, Visualizing, and Computing on Surfaces of Evolution," *IEEE Computer Graphics and Applications*, cover page and pp. 31-41 (Jul. 1988).

Hayashi, T. et al., "A Computerized System for Analyzing Occlusal Relations During Mandibular Movements," *The International Journal of Prosthodontics*, vol. 7, No. 2, cover page and pp. 108-114 (Mar./Apr. 1994).

Hibi, H. et al., "An Optical System for Measuring Inclination and area of Occlusal Facets," *Journal of Oral Rehabilitation*, vol. 24, No. 9, pp. 673-677 (Sep. 1997).

Jones, M. et al., "A Validated Finite Element Method Study of Orthodontic Tooth Movement in the Human Subject," *Journal of Orthodontics*, vol. 28, No. 1, pp. 29-38 (Mar. 2001) (1 page abstract).

Kimura, H. et al., "Three-Dimensional Shape Measurement of Teeth. On the Measurement by the Laser Displacement Meter which is able to Move on Z-direction," *Journal of the Japanese Society for Dental Materials and Devices*, vol. 8, No. 6, pp. 877-882 (Nov. 1989) (1 page abstract).

Kimura, H. et al., "Three-Dimensional Shape Measurement of Teeth. Measurement of Tooth Model by Tilting Method by Means of the Double Sensor Laser Displacement Meter, and the Simulation of Occlusion," *Journal of the Japanese Society for Dental Materials and Devices*, vol. 9, No. 4, pp. 679-686 (Jul. 1990) (1 page abstract).

Kunii, T. et al., "Articulation Simulation for an Intelligent Dental Care System," *University of Aizu*, vol. 15, No. 3, pp. 181-188 (1994).

Kuroda, T. et al., "Three-dimensional dental cast analyzing system using laser scanning," *American Journal of Orthodontics and Dentofacial Orthopedics*, vol. 110, No. 4, cover page, table of contents, and pp. 365-369 (Oct. 1996).

Larkin, J., "Means for measuring the interocclusal distance," *The Journal of Prosthetic Dentistry*, vol. 17, No. 3, pp. 247-250 (Mar. 1967).

Laurendeau, D. et al., "A Computer-Vision Technique for the Acquisition and Processing of 3-D Profiles of Dental Imprints: An Application in Orthodontics," *IEEE Transactions on Medical Imaging*, vol. 10, No. 3, pp. 453-461 (Sep. 1991).

Leinfelder, K. et al., "A new method for generating ceramic restorations: a CAD-CAM System," *Journal of the American Dental Association*, vol. 118, cover page and pp. 703-707 (Jun. 1989).

OrthoCad, "Virtual Set-Up," OrthoCad advertisement, 1 page (admitted by Applicants as prior art as of the filing date).

Palmer, R. "CAD/CAM Dental Technology's Future?," *Dental Lab Products*, pp. 14-18 (May/Jun. 2002).

Rekow, D., "Computer-aided design and manufacturing in dentistry; a review of the state of the art," *The Journal of Prosthetic Dentistry*, vol. 58, No. 4, cover page and pp. 513-516 (Oct. 1987).

Rodger, J. et al., "Choosing Rendering Parameters for Effective Communication of 3d Shape," *IEEE Computer Graphics and Applications*, pp. 20-28 (Mar./Apr. 2000).

Sakaguchi, R. et al., "Digital Imaging of Occlusal Contacts in the Intercuspal Position," *Journal of Prosthodontics*, vol. 3, No. 4, pp. 193-197 (Dec. 1994).

Santler, G. et al., "Indications and Limitations of Three-Dimensional Models in Cranio-Maxillofacial Surgery," *Journal of Cranial-Maxillo-Facial Surgery*, vol. 26, No. 1, pp. 11-16 (Feb. 1998) (1 page abstract).

Schirmer, U. et al., "Manual and Computer-Aided Space Analysis: A Comparative Study," *American Journal of Orthodontics and Dentofactial Orthopedics*, vol. 112, No. 6, pp. 676-680 (Dec. 1997) (1 page abastract).

Siirilä, H. et al., "A Photographic Method for Measuring Interocclusal Clearance," *Suom. Hammaslääk., Toim.* vol. 66, No. 3, pp. 177-182 (1970), English Summary, p. 181.

Tekscan, The T-Scan II "The Future Force in Occlusal Diagnostics", Online Tekscan System brochure, Retrieved from http://www.tekscan.com/dental/system.html, pp. 1-9 (Oct. 3, 2002).

Tekscan, T-Scan II "Dental Division Overview", Online Tekscan System brochure, Retrieved from http://tekscan.com/dental.html, pp. 1-2, (Oct. 3, 2002).

M. Naeije et al., OKAS-3D: Optoelectronic Jaw Movement Recording System with Six Degrees of Freedom; Medical & Biological Engineering & Computing, Sep. 1995, 33, 683-688.

Travers et al., *Associations Between Incisor and Mandibular Condylar Movements During Maximum Mouth Opening in Humans*; Archives of Oral Biology 45 (2000); Nov. 1, 1999; pp. 270-275.

Wenzel et al., "Accuracy of caries diagnosis in digital images from charge-coupled device and storage phosphor systems: an in vitro study," *Dentomaxilofac. Radiol*.(1995) 24 (4): 250-254.

Sohmura et al., "Use of CAD/CAM system to fabricate dental prostheses. Part 1: CAD for a clinical crown restoration," *The International Journal of Prosthodontics* (1995) 8 (3): 252-258.

Seymour et al., "Assessment of shoulder dimensions and angles of porcelain bonded to metal crown preparations," *The Journal of Prosthetic Dentistry* (1996) 75: 406-411.

Deng et al., "Occlusal contact changes before and after orthodontic treatment of a group of child & adolescent patients with TMJ disturbance," *Australian Orthodontic Journal* (1995) 13 (4): 231-237.

* cited by examiner

SYSTEM AND METHOD FOR GENERATING AN ELECTRONIC MODEL FOR A DENTAL IMPRESSION HAVING A COMMON COORDINATE SYSTEM

TECHNICAL FIELD

This application relates in general to a method and apparatus for providing electronic models from scanning physical objects, and more particularly to a method and apparatus for generating an electronic model for a dental impression having a common coordinate system.

BACKGROUND OF THE INVENTION

The use of computer-aided manipulating of electronic models that correspond to physical objects has become more prevalent as the capabilities of computer processing systems has increased. This manipulation began with the modeling and representing of a single physical object. In some cases, a physical object has been scanned to generate an electronic model corresponding to the physical object. Once a single physical object has been modeled, the development of these systems moved to the generation of electronic models for multiple objects that are physically related. These systems attempt to permit a user to manipulate these multiple objects in a manner that corresponds to the manner in which the physical objects interact with each other in the physical world.

One such application of this electronic modeling technology is in the dental field in which electronic models are generated that correspond to physical models made from impressions of teeth in a human mouth. These physical models for patient's teeth have been used by dentists and other dental health professionals to study the interaction of the opposing jaws before, during, and after treatment plan is implemented. Examples of uses of these electronic models within the dental field included: U.S. Provisional Patent Application entitled: "METHOD AND APPARATUS FOR COMPUTER GENERATION OF ELECTRONIC MODEL IMAGES", Ser. No. 60/351,270, filed Jan. 22, 2002, now U.S. application entitled, "METHOD AND APPARATUS FOR COMPUTER GENERATION OF ELECTRONIC MODEL IMAGES", Ser. No. 10/350,302, filed Jan. 22, 2003; U.S. patent application entitled, "METHOD AND APPARATUS FOR ELECTRONIC DELIVERY OF DENTAL IMAGES", Ser. No. 09/846,037, filed Apr. 29, 2001; U.S. patent application entitled, "METHOD AND APPARATUS FOR CONSTRUCTING CROWNS, BRIDGES AND IMPLANTS FOR DENTAL USE", Ser. No. 10/429,288, filed May 2, 2003; U.S. Provisional Patent Application entitled, "METHOD AND APPARATUS FOR ELECTRONICALLY SIMULATING JAW FUNCTION", Ser. No. 60/376,111, filed Apr. 29, 2002, now U.S. patent application entitled "METHOD AND APPARATUS FOR ELECTRONICALLY SIMULATING JAW FUNCTION", Ser. No. 10/426,253, filed Apr. 29, 2003; U.S. Provisional Patent Application entitled, "METHOD AND APPARATUS FOR ELECTRONICALLY GENERATING A COLOR DENTAL OCCLUSION MAP WITHIN ELECTRONIC MODEL IMAGES", Ser. No. 60/376,091, filed Apr. 29, 2002, now U.S. patent application entitled "METHOD AND APPARATUS FOR ELECTRONICALLY GENERATING A COLOR DENTAL OCCLUSION MAP WITHIN ELECTRONIC MODEL IMAGES", Ser. No. 10/426,252, filed Apr. 29, 2003; and U.S. patent application entitled "METHOD AND APPARATUS USING A SCANNED IMAGE FOR AUTOMATICALLY PLACING BRACKET IN PRE-DETERMINED LOCATIONS", Ser. No. 10/429,262, filed May 2, 2003, which is a continuation-in-part of U.S. patent application entitled, "METHOD AND APPARATUS USING A SCANNED IMAGE FOR MARKING BRACKET LOCATIONS", Ser. No. 10/349,559, filed Jan. 22, 2003, which claims priority to U.S. Provisional Application entitled, "METHOD AND APPARATUS USING A SCANNED IMAGE FOR MARKING BRACKET LOCATIONS", Ser. No. 60/351,311, filed Jan. 22, 2002. Additionally, these electronic models may be used as part of data processing of images in support of the development of these treatment plans. Examples include: U.S. Provisional Patent Application entitled, "METHOD AND APPARATUS FOR AUTOMATICALLY DETERMINING THE LOCATION OF INDIVIDUAL TEETH WITHIN ELECTRONIC MODEL IMAGES", Ser. No. 60/351,271, filed Jan. 22, 2002, now U.S. patent application entitled, "METHOD AND APPARATUS FOR AUTOMATICALLY DETERMINING THE LOCATION OF INDIVIDUAL TEETH WITHIN ELECTRONIC MODEL IMAGES", Ser. No. 10/350,304, filed Jan. 22, 2003.

Within each of these applications, the scanning of the dental impression of a patient's mouth produces two separate electronic models that need to be integrated into a single frame of reference if the two models are to be used to interact with each other. This single frame of reference corresponds to a single coordinate system in which all known points in the two electronic models for the upper and lower jaws are specified in a single coordinate system. As such, a simple mechanism to determine common points in each of the two electronic model coordinate systems such that the translation of one coordinate system into the other coordinate system may be performed easily. In prior art systems, the two electronic models were separately generated after which a user would identify common points in the opposing model. Such a system is prone to error of a user in selecting the common points and as such is not readily repeatable. As such, there is a further need for a system and method to automatically determine a common coordinate system for the two electronic models for a patient's mouth when the two physical models are scanned. These and numerous other disadvantages of the prior art necessitate the need for the method and apparatus provided by the present invention.

SUMMARY OF THE INVENTION

This application relates in general to a method and apparatus for generating an electronic model for a dental impression having a common coordinate system. One possible embodiment of the present invention is a system for generating an electronic model for a dental impression having a common coordinate system. The system includes two scanning apparatus for positioning physical objects within a scanning device when generating an electronic model corresponding to each of the physical objects; a data processing system for processing the electronic models corresponding to each of the physical objects to possess polygonal mesh representations of the physical objects within a common coordinate system. The scanning apparatus comprises a scanning base plate module for coupling the scanning apparatus to the scanning device and a physical model plate module to coupling the physical object to the scanning base plate module within a coordinate system of the scanning device.

Another aspect of the present invention is a method for generating an electronic model for a dental impression having a common coordinate system. The method mounts physical models onto corresponding scanning apparatus, the scanning apparatus positions the physical models within a coordinate system of a scanning device; generates an electronic model for each physical model, the electronic models correspond to polygonal mesh representations of scanned position data; positions each of the scanning apparatus into a desired position in which the physical models are positioned relative to each other as the objects corresponding to the physical models interact with each other to generate a composite scanning apparatus; scans a reference point on one or more scanning apparatus within the combined scanning apparatus that are not coupled to the scanning device; and transforms the electronic models corresponding to the objects having scanning apparatus not coupled to the scanning device to generate composite electronic models in a common coordinate system.

DETAILED DESCRIPTION OF THE PREFERRED EMBODIMENT

Figure 1A:
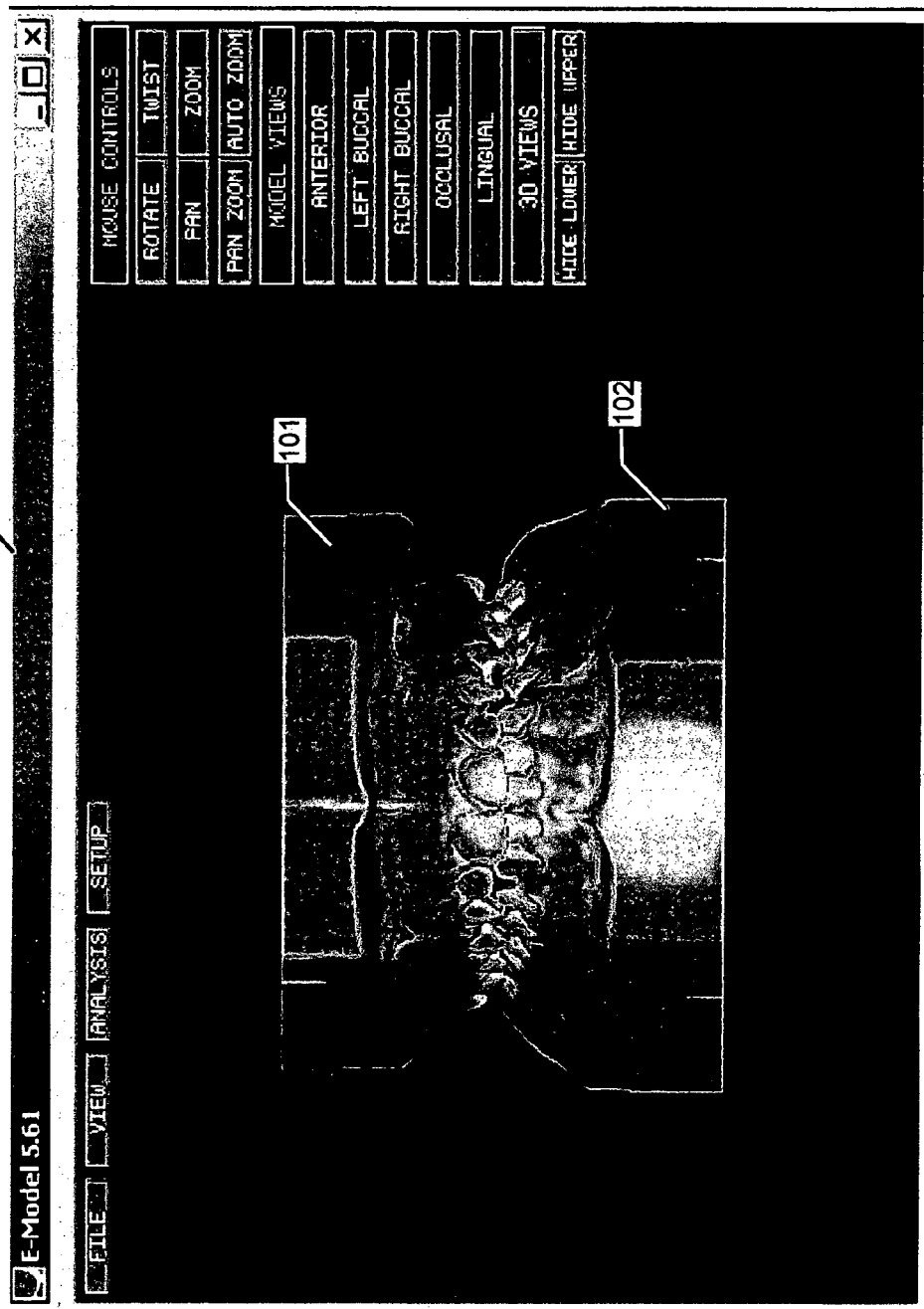
FIG. 1a illustrates an example embodiment of an electronic model for an upper and lower jaw impression electronically interacting with each other according to one possible embodiment of the present invention.

This application relates in general to a method and apparatus for generating an electronic model for a dental impression having a common coordinate system. In the following detailed description of exemplary embodiments of the invention, reference is made to the accompanied drawings, which form a part hereof, and which is shown by way of illustration, specific exemplary embodiments of which the invention may be practiced. These embodiments are described in sufficient detail to enable those skilled in the art to practice the invention, and it is to be understood that other embodiments may be utilized, and other changes may be made, without departing from the spirit or scope of the present invention. The following detailed description is, therefore, not to be taken in a limiting sense, and the scope of the present invention is defined only by the appended claims.

Throughout the specification and claims, the following terms take the meanings explicitly associated therein, unless the context clearly dictates otherwise. The term "connected" means a direct connection between the items connected, without any intermediate devices. The term "coupled" means either a direct connection between the items connected, or an indirect connection through one or more passive or active intermediary devices. The term "circuit" means either a single component or a multiplicity of components, either active and/or passive, that are coupled together to provide a desired function. The term "signal" means at least one current, voltage, or data signal. Referring to the drawings, like numbers indicate like parts throughout the views.

FIG. 1a illustrates an example embodiment of an electronic model for an upper and lower jaw impression electronically interacting with each other according to one possible embodiment of the present invention. A computer-generated image 100 of a pair of electronic models corresponding to a patient's upper jaw 101 and lower jaw 102 are shown. These two models are generated separately and then positioned together to allow the interaction of the opposing teeth present in the upper jaw 101 and the lower jaw 102 electronic models. This interaction of the upper jaw 101 and the lower jaw 102 cannot occur until the coordinate systems of the two electronic models are combined into a single coordinate system.

Figure 1B:
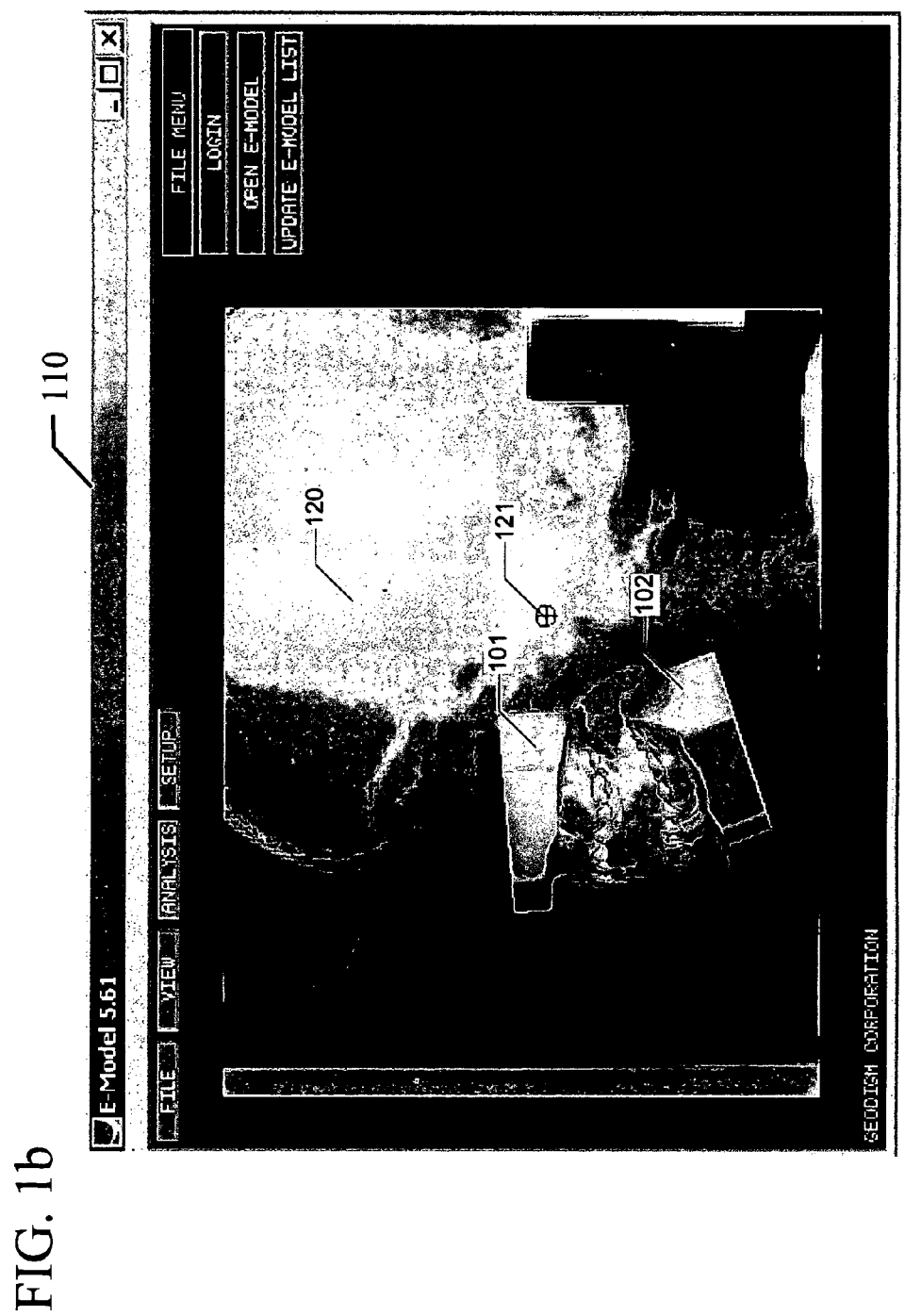
FIG. 1b illustrates an example embodiment of an electronic model of a dental impression used to demonstrate articulation of a jaw and corresponding teeth according to one possible embodiment of the present invention.

FIG. 1b illustrates an example embodiment of an electronic model of a dental impression used to demonstrate articulation of a jaw and corresponding teeth according to one possible embodiment of the present invention. In this example embodiment 110, the electronic models for the upper jaw 101 and the lower jaw 102 are super imposed upon an x-ray of the patient's skull 120 to allow the two electronic models to be moved relative to each other about a point of rotation for the jaw 121 in a manner that is consistent with the actual geometry of a patient as shown in the x-ray 120. This movement and interaction of the upper jaw 101 and the lower jaw 102 also require the use of a common coordinate system for the electronic models for the upper jaw 101 and the lower jaw 102. Additional details regarding the use of electronic models in the simulation of teeth and jaw movement relative to each other may be found within U.S. Provisional Patent Application entitled, "METHOD AND APPARATUS FOR ELECTRONICALLY SIMULATING JAW FUNCTION", Ser. No. 60/376,111, filed Apr. 29, 2002, now U.S. patent application entitled, "METHOD AND APPARATUS FOR ELECTRONICALLY SIMULATING JAW FUNCTION", Ser. No. 10/426,253, filed Apr. 29, 2003, both of which are incorporated herein in their respective entireties.

Figure 2:
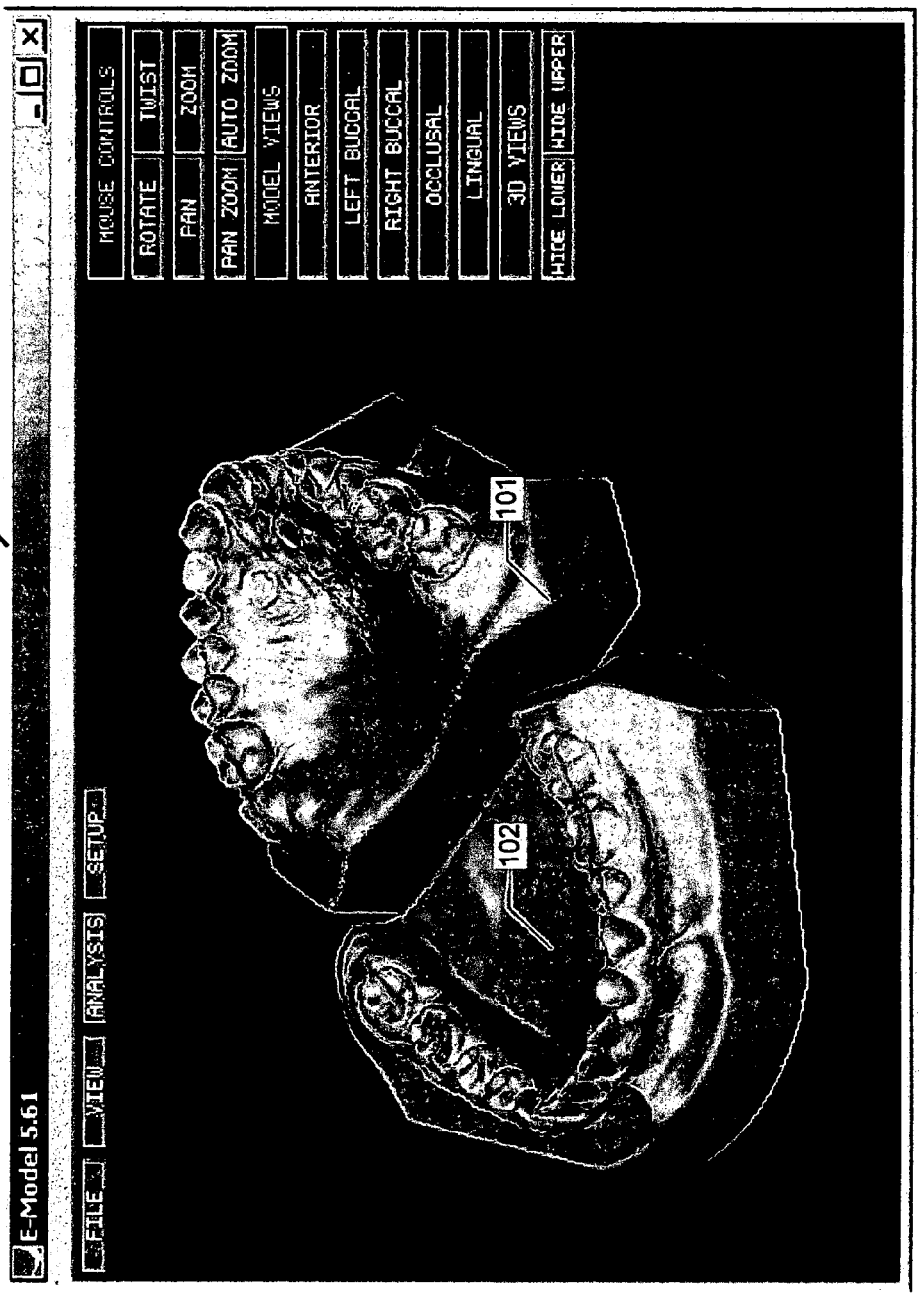
FIG. 2 illustrates another example embodiment of an electronic model for an upper and lower jaw impression electronically interacting with each other according to one possible embodiment of the present invention.

FIG. 2 illustrates another example embodiment of an electronic model for an upper and lower jaw impression electronically interacting with each other according to one possible embodiment of the present invention. In this embodiment 200, the upper jaw 101 and the lower jaw 102 are shown in a position that corresponds to the position in which the two physical models may be scanned together. In this embodiment 200, the two models are shown with a flat surface of the base elements in which the impressions for the teeth are mounted. The two flat surfaces are typically shown in a co-planar arrangement with some physical separation for the two models. While the side surfaces of the base elements contain a few co-planar surfaces that allow the registration of the models in various dimensions, the vertical Z-axis for the two models is not radially detectable. As such, additional steps must be taken to translate the positions in the two electronic models into a single coordinate system. These operations must occur before the two models 101-102 may be manipulated as opposing teeth and jaws.

Figure 3:
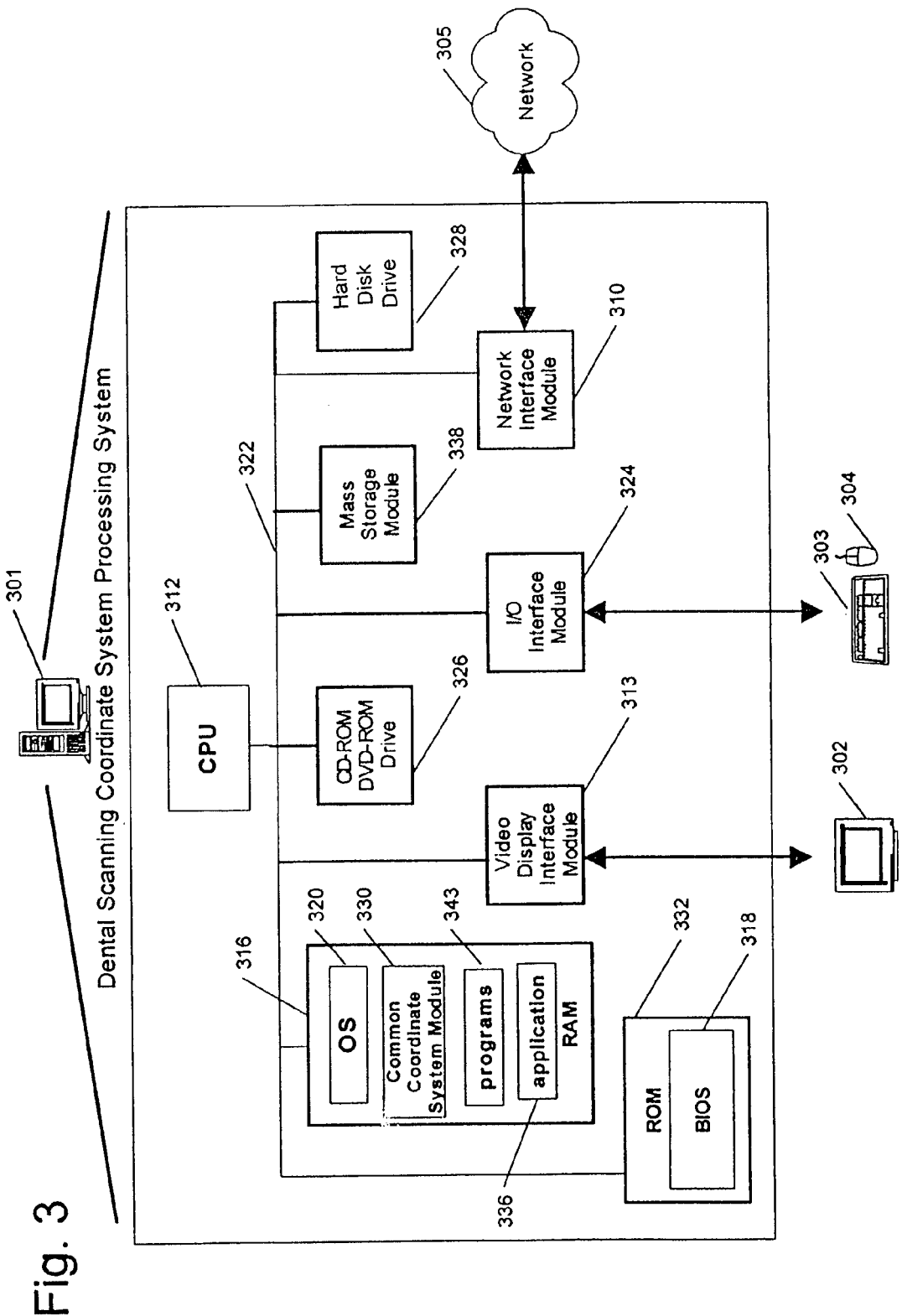
FIG. 3 illustrates a computing system that may be used to construct various computing systems that may be part of a distributed processing and communications system according to one embodiment of the present invention.

FIG. 3 illustrates a computing system that may be used to construct various computing systems that may be part of a distributed processing and communications system according to one embodiment of the present invention. In an exemplary embodiment of a processing system 301, computing system 301 is operative to provide a dental scanning coordinate processing system. Those of ordinary skill in the art will appreciate that the dental scanning coordinate processing system 301 may include many more components than those shown with reference to a computing system 301 shown in FIG. 3. However, the components shown are sufficient to disclose an illustrative embodiment for practicing the present invention. Those of ordinary skill in the art will appreciate that a network interface unit 310 includes the necessary circuitry for connecting dental scanning coordinate system processing system 301 to a network of other computing systems 305, and is constructed for use with various communication protocols including the TCP/IP protocol. Typically, network interface unit 310 is a card contained within neural network training and data collection system.

Dental scanning coordinate system processing system 301 also includes processing unit 312, video display adapter 314, and a mass memory 316, all connected via bus 322. The mass memory generally includes RAM 416, ROM 432, and one or more permanent mass storage devices, such as hard disk drive 328, a tape drive, CD-ROM/DVD-ROM drive 326, and/or a floppy disk drive. The mass memory stores operating system 320 for controlling the operation of dental scanning coordinate processing system 301. It will be appreciated that this component may comprise a general purpose server operating system as is known to those of ordinary skill in the art, such as UNIX, MAC OS™, LINUX™, OR Microsoft WINDOWS NT®. Basic input/output system ("BIOS") 318 is also provided for controlling the low-level operation of processing system 301.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing a software development and neural network analysis and training system. More specifically, the mass memory stores applications including common coordinate system application program 330, programs 343, and similar data processing applications 336. Common coordinate system application program 330 includes computer executable instructions which, when executed by computer 301 to perform the logic desired herein.

Dental scanning coordinate system processing system 301 also comprises input/output interface 324 for communicating with external devices, such as a mouse 304, keyboard 303, scanner, or other input devices not shown in FIG. 3. Likewise, a dental scanning coordinate system processing system 301 may further comprise additional mass storage facilities such as CD-ROM/DVD-ROM drive 326 and hard disk drive 328. Hard disk drive 328 is utilized by Dental scanning coordinate system processing system 301 to store, among other things, application programs, databases, and program data used by common coordinate system application program 330.

Figure 4:
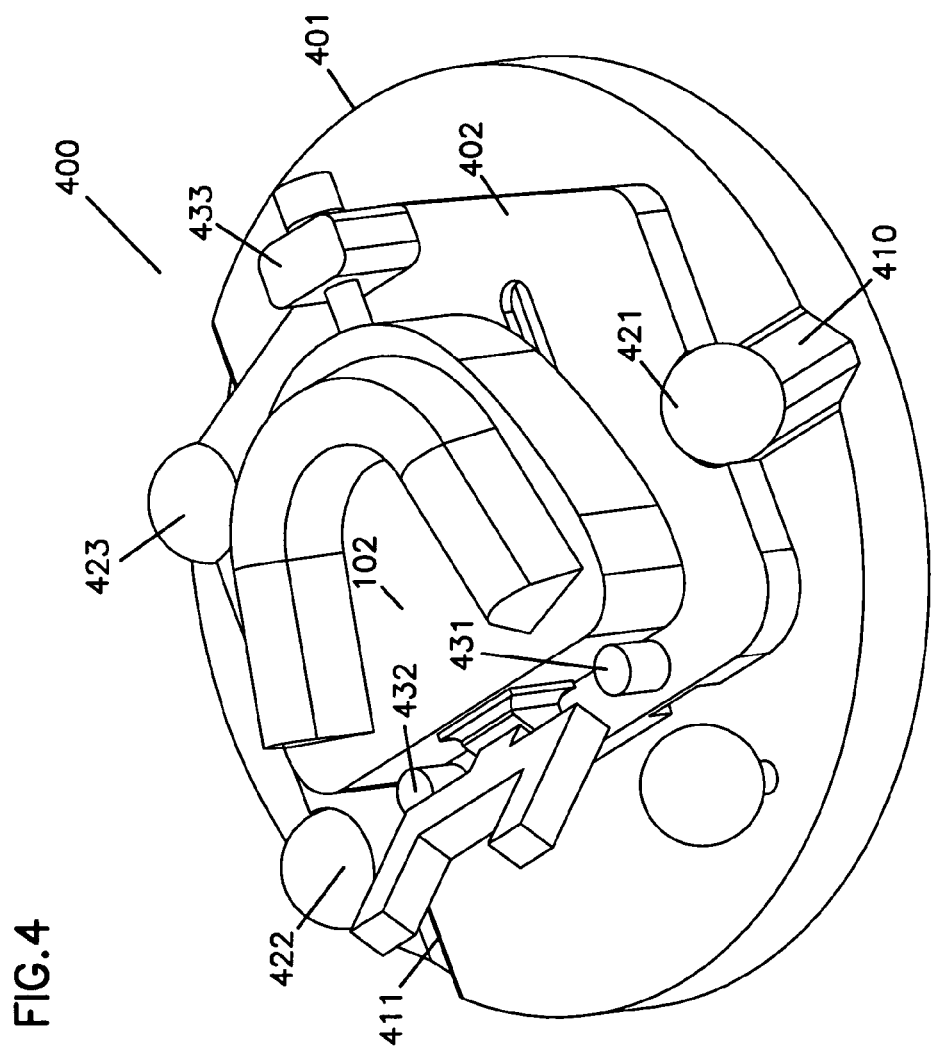
FIG. 4 illustrates a lower jaw dental impression physical model scanning plate apparatus according to an example embodiment of the present invention.

FIG. 4 illustrates a lower jaw dental impression physical model scanning apparatus according to an example embodiment of the present invention. The apparatus 400 is used to scan a physical impression model for a jaw. In this example, a lower jaw 102 physical model is shown. The apparatus comprises a scanning base plate module 401 and a physical model plate module 402. The scanning base plate module 401 is mounted onto a scanning device such that a model that is scanned while attached to the apparatus 400 is located within a known location of the scanning system coordinate system. The scanning system is calibrated to know the position of the scanning base plate 401. The scanning base plate module 401 contains an x-axis alignment channel 411 and a y-axis alignment channel 410. These two alignment channels are located on the scanning base plate module 401 in a perpendicular and a co-planar within the plane defined by the top surface of the scanning base plate module 401. These two alignment channels are generally v-shaped such that the vertex of the channel defines the deepest point within the channel.

The physical model plate module 402 comprises a y-axis channel alignment sphere 421, a first x-axis channel alignment sphere 422, and a second x-axis channel alignment sphere 423. The physical model plate module 402 also comprises a set of physical model attachment devices 431-433 that are used to secure the physical model 102 into a fixed position on the physical model plate module 402. The y-axis channel alignment sphere 421, the first x-axis channel alignment sphere 422, and the second x-axis channel alignment sphere 423 are defined by a radius corresponding to the size of the two alignment channels within the scanning base plate module 401. These three spheres engage the two alignment channel to position the physical model plate module 402 at a known and repeatable position relative to the scanning base plate model 401. As such, a scan of a physical model 102 will be at a known position relative to the scanning device. This aligned position occurs because the first x-axis channel alignment sphere 422 and the second x-axis channel alignment sphere 423 position the physical module plate module 402 at a known position relative to the scanning base plate module 401 in the x-axis dimension. Similarly, the y-axis channel alignment sphere 421 engaging the y-axis alignment channel 410 to position the physical module plate module 402 at a known position relative to the scanning base plate module 401 in the y-axis dimension. The combination of the two alignment channels 410-411 and the three alignment spheres 421-423 allows the physical model plate module 402 to be located at a single position within a plate parallel to the top of the scanning plate module 401.

The same arrangement is used for the opposing physical model 101 using a second physical model scanning apparatus. From these two apparatus, the two separate electronic models are generated having two separate coordinate systems. These two separate coordinate systems are combined as discussed below to place all of the points used to define the two electronic models within a single coordinate system. Additional details regarding the scanning of physical models to generated the electronic models may be found in commonly assigned U.S. Provisional Patent Application entitled, "METHOD AND APPARATUS FOR COMPUTER GENERATION OF ELECTRONIC MODEL IMAGES", Ser. No. 60/351,270 filed Jan. 22, 2002, now U.S. patent application entitled, "METHOD AND APPARATUS FOR COMPUTER GENERATION OF ELECTRONIC MODEL IMAGES", Ser. No. 10/350,302, filed Jan. 22, 2003, both of which are incorporated herein in their entirety.

Figure 5:
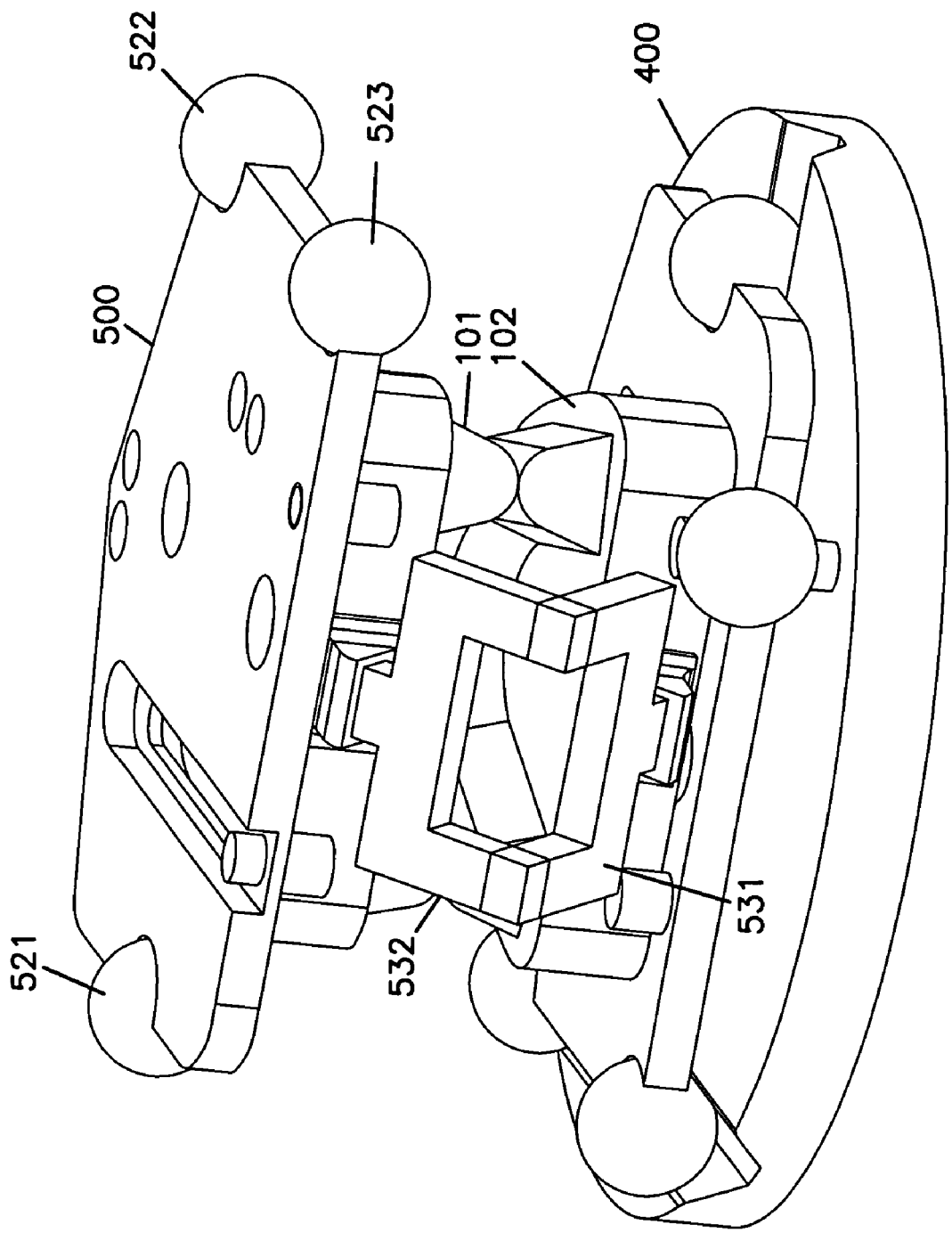
FIG. 5 illustrates an upper and a lower jaw dental impression physical model scanning plate apparatus according to an example embodiment of the present invention.

FIG. 5 illustrates an upper and lower jaw dental impression physical model scanning plate apparatus according to an example embodiment of the present invention. In this example embodiment, the physical model scanning apparatus 400 discussed in reference to FIG. 4 is shown. A second physical model scanning apparatus 500 that contains the opposing physical model for an upper jaw 101 is also shown. The second physical model scanning apparatus 500 operates identically to the apparatus 400 discussed in reference to FIG. 4 for a second physical model.

In this example embodiment, each apparatus 400, 500 also contain an articulation member 531,532. These two articulation members are coupled together to position the upper apparatus 500 at a position relative to the lower apparatus 400 that simulates the interaction of the upper jaw physical model 101 and the lower jaw physical model 102. By manipulating the arrangements of the two articulation members, the two physical models 101, 102 may be positioned into any desired position relative to each other. The desired position may be defined by a user who moved the two apparatus 400, 500 until the two jaw models are in the desired position relative to each other. In other embodiments, additional items such as a bite wax impression obtained from the patient may be inserted between the two physical models to position them in a desired position corresponding to the geometry of the patient's mouth.

It is contemplated herein that other and/or additional records of patient's bites could be utilized in connection with developing and describing a patient's jaw motion. For example, centric, occlusion centric relation, protrusive, and lateral excursion (left and/or right) might be used to determine jaw motion. In addition, the system could manipulate the jaw image between established positions to obtain an electronic simulation of jaw motion (e.g., digital articulation).

Once the two apparatus 400-500 are positioned in a desired position, the combined apparatus may be scanned while attached to the scanning device within the coordinate system used in generating the electronic model 102 for the lower jaw to determine the position of the upper apparatus 500 within the same coordinate system. When the scanning is performed for the combined apparatus, only the location of one of the alignment spheres 521-523 need to be determined. From this additional information, the location of any point on the electronic model 101 for the upper jaw may be expressed in terms of the coordinate system used to define the electrode model 102 for the lower jaw. This coordinate transformation is illustrated in reference to FIG. 6 below.

Figure 6:
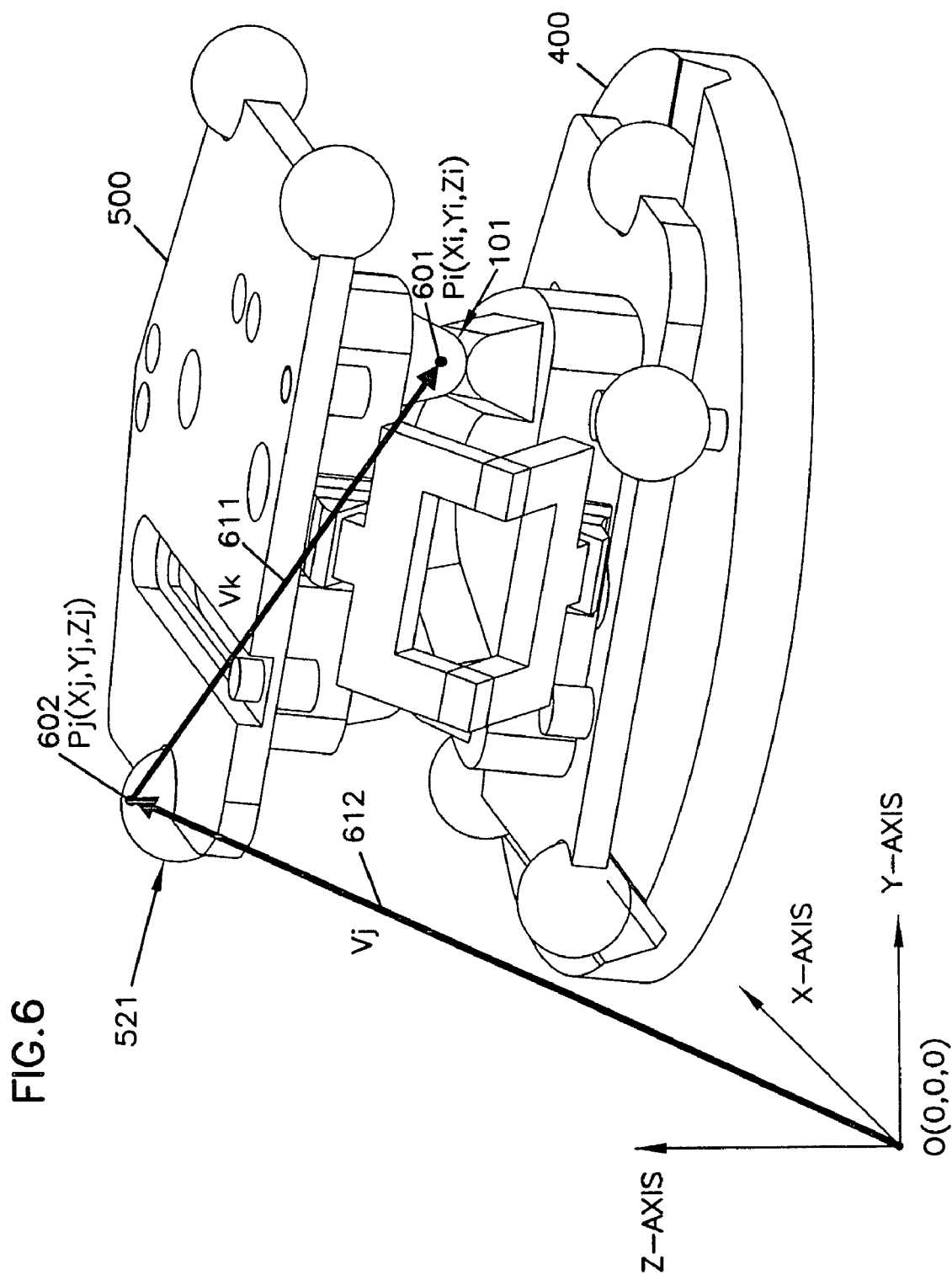
FIG. 6 illustrates a spatial transformation for a point located on an upper electronic model from its own coordinate system to a single coordinate system.

FIG. 6 illustrates a spatial transformation for a point located on an upper electronic model from its own coordinate system to a single coordinate system. A point Pi 601 on the electronic model for the upper jaw 101 is defined in terms of a common coordinate system having an origin O. The point Pi 601 is defined as having a position in this common coordinate system Pi=(Xi, Yi, Zi).

In order to define the values that comprise Pi, one needs to combine the values of vector Vj 612 with vector Vk 611. Vj 611 is defined in terms of the coordinate system used when the electronic model for the upper jaw was scanned. This vector is known since both the point Pi 601 is known in the coordinate system used when the electronic model for the upper jaw was scanned and the point Pj 602 is known as the top point on the sphere 521 in the same coordinate system. This point is known as a fixed point in the coordinate system when the alignment spheres are engaged with the alignment channels.

Vector Vj 612 is the value for the location of this top point on sphere 521 when the combined apparatus is scanned after the two physical models are moved into the desired position. These two vectors, when added together for each location on the upper electronic model 101, transforms all of the coordinates from the two separate coordinate systems into a single coordinate system.

Figure 7:
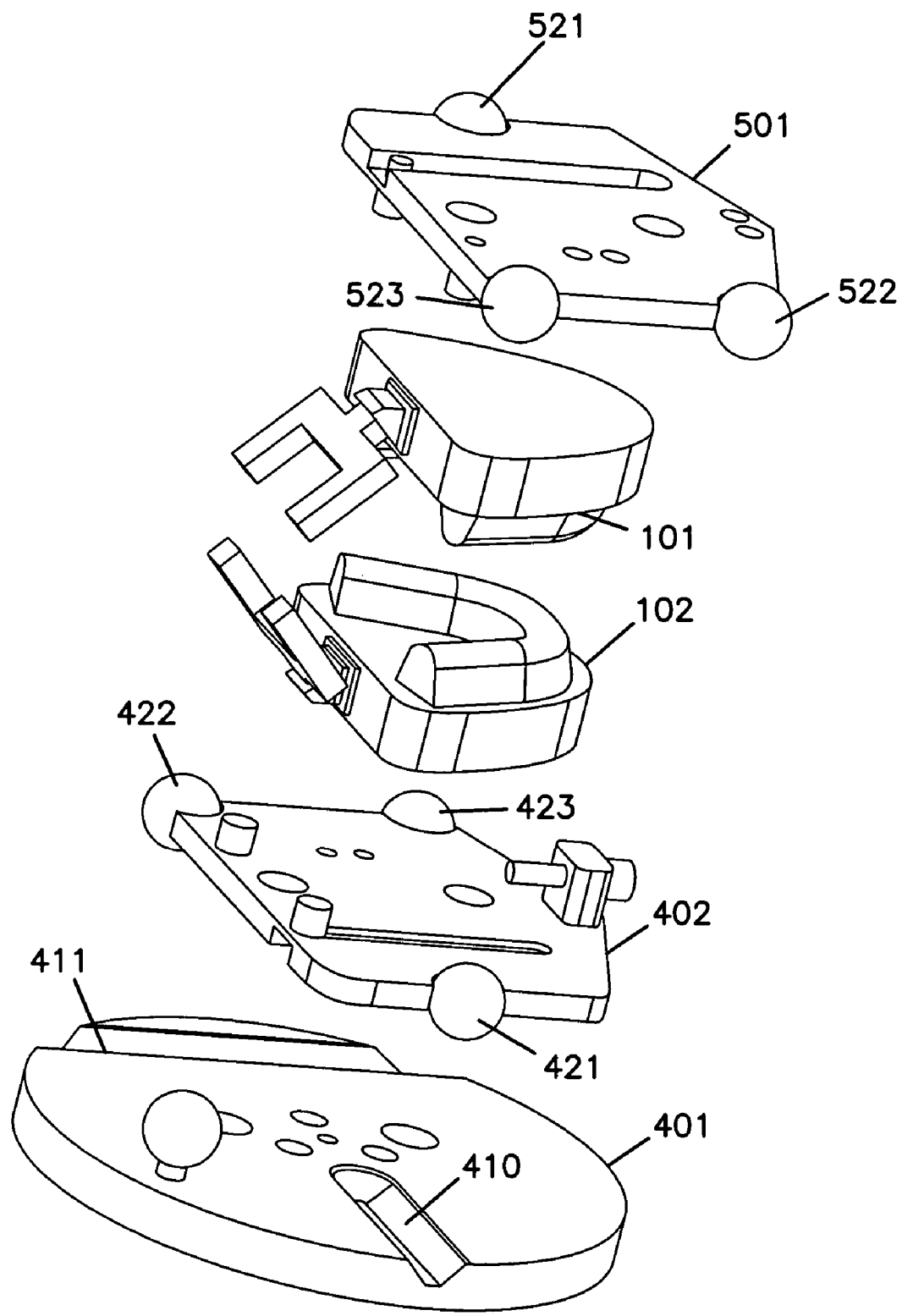
FIG. 7 illustrates an exploded view for the upper and lower jaw dental impression physical model scanning plate apparatus according to an example embodiment of the present invention.

FIG. 7 illustrates an exploded view for the upper and lower jaw dental impression physical model scanning plate apparatus according to an example embodiment of the present invention. The exploded view includes the scanning base plate module 401 corresponding to the electronic model generated for the lower jaw model 102; the physical model plate module 402 including its three alignment spheres 421-423, and the physical module corresponding to the lower jaw 102. The exploded view of FIG. 7 also includes the physical model corresponding to the upper jaw 101 and the physical model plate module 501 including its three alignment spheres 521-523 used to generate the electronic model for the upper jaw 101. These components work together as discussed above to generate a composite electronic model for the upper and low jaw of a patient within a common coordinate system.

Figure 8:
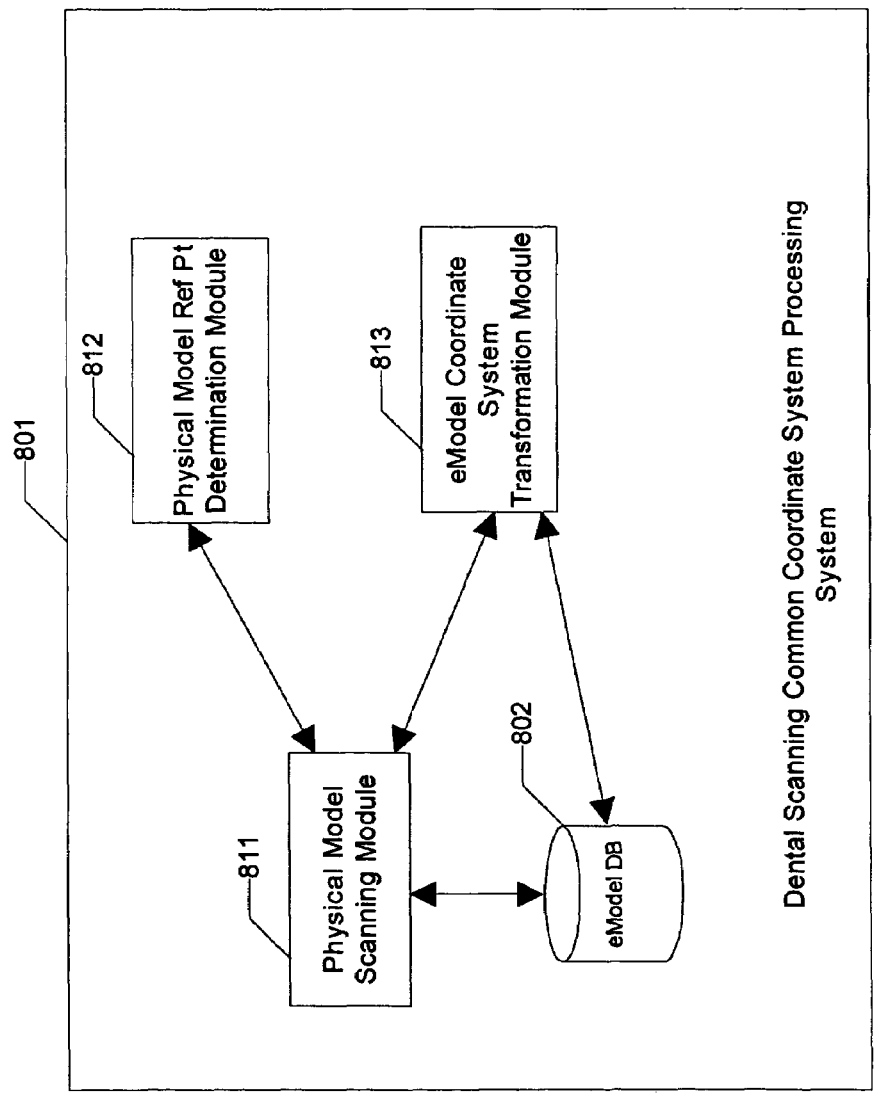
FIG. 8 illustrates a set of processing modules used within a processing system that is part of a system for generating an electronic model for dental impression having a common coordinate system according to another example embodiment of the present invention.

FIG. 8 illustrates a set of processing modules used within processing system that is part of a system for generating an electronic model for a dental impression having a common coordinate system according to another example embodiment of the present invention. A dental scanning common coordinate system processing system 801 comprises a set of data processing modules that are used to generate the separate upper and low jaw electronic models and combine the data from these two models into a common coordinate system. The dental scanning common coordinate system processing system 801 includes a physical model scanning module 811, a physical model reference point determination module 812, and an electronic model coordinate system transformation module 813. The dental scanning common coordinate system processing system 801 also includes a electronic model database 802 for storing and retrieving electronic model data as needed from data storage. In most embodiments, the database is maintained within mass storage devices attached to a programmable processing system.

The physical model scanning module 811 interacts with a laser scanning device to obtain a set of position data points obtained from the scanning of a physical model. This processing system 801 performs all of the processing necessary to reduce this data of location points to an electronic model defined in a polygonal mesh. These electronic models generated by this processing module 801 may be stored within the electronic model database 802 for later use. These electronic models may also be passed to the physical model reference point determination module 812, for further processing.

The physical model reference point determination module 812 interacts with the laser scanning device to obtain the location of the reference data point Pj 602 as discussed above with respect to FIG. 6 on a composite apparatus. This reference data point Pj 602 is used to generate the transformation vector Vj 612 that is used to generate the transformed location data when location data points from an upper jaw electronic model are processed to express location information within a common coordinate system.

The electronic model coordinate system transformation module 813 uses the vector Vj 612 determined within the physical model reference point determination module 812 to generate the coordinate data values for each point in an electronic model of an upper jaw 101 within the common coordinate system. This module 813 may be used to transform every data point within an electronic model before the updated electronic model is stored in the electronic model database 802. Alternatively, this module 813 may be used to transform the data points within an area/region of interest in the electronic model to allow the process to be completed more quickly. One skilled in the art will recognize that many different processing mechanisms for generating and applying the transformation vector Vj 612 without deviating from the spirit and scope of the present invention as recited within the attached claims.

Figure 9:
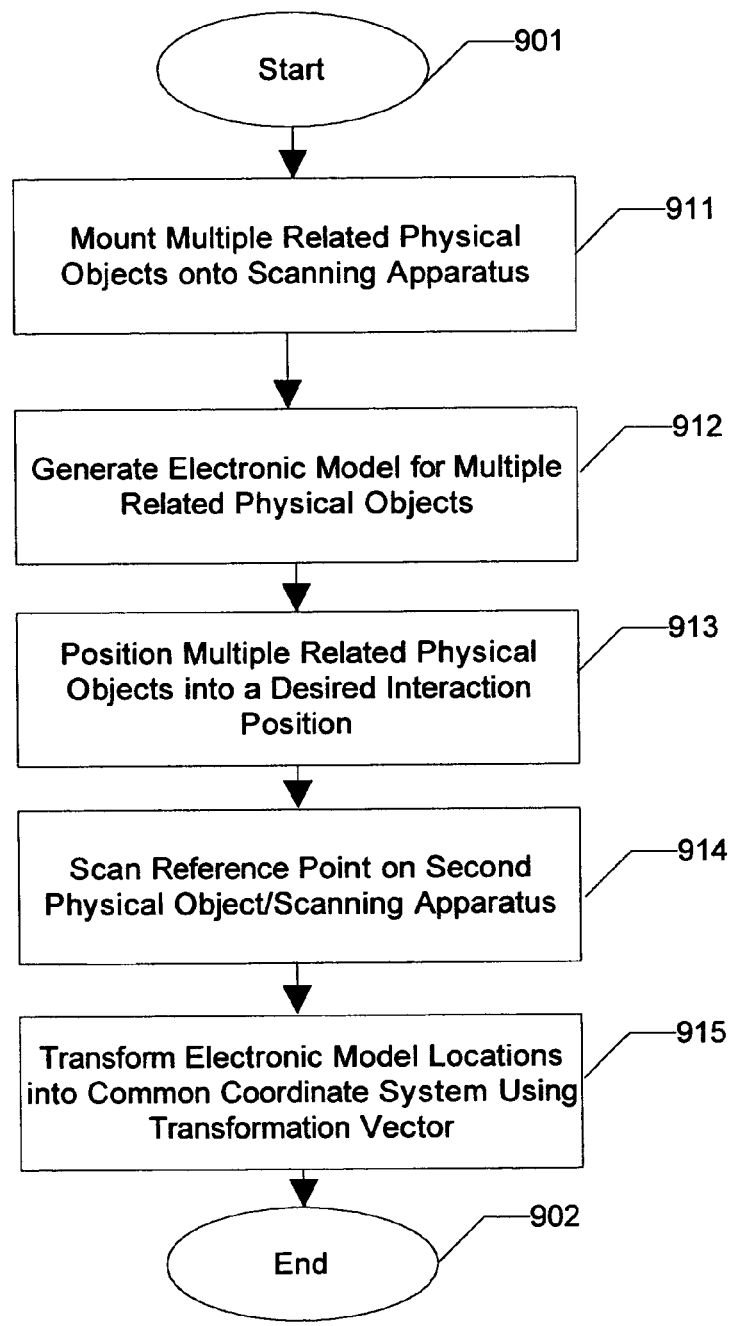
FIG. 9 illustrates an example operation flow for a system for generating an electronic model for a dental impression having a common coordinate system according to one possible embodiment of the present invention.

FIG. 9 illustrates an example operation flow for a system for generating an electronic model for a dental impression having a common coordinate system according to one possible embodiment of the present invention. The process begins 901 and proceeds to operation 911 in which the various physical models are mounted on the scanning apparatus that is part of a scanning device. In completing this operation 911, the physical models are located within the coordinate system of the scanning device for scanning. Next, operation 912 scans the physical models and then generates the electronic models corresponding to the various physical models. These electronic models are expressed as a polygonal mesh that corresponds to the outside surface of the physical objects.

Operation 913 then positions the various physical models into desired positions in which the physical models interact with each other in the same way that the corresponding physical objects interact with each other. In the dental model processing, the upper and lower physical models are positioned into a position that represents the relationship of the upper and lower jaw of a patient. This positioning may occur in different ways as discussed above with reference to FIG. 6 without deviating from the spirit and scope of the present invention as recited in the attached claims.

Once the physical models are positioned into the desired locations, operation 914 scans one or more reference points on the combined scanning apparatus. This scanning may include the scanning of the alignment spheres on a physical model plate module 502 for an upper object to obtain a point of known position on the upper electronic model that is also known within the coordinate system for the upper object when it was scanned individually. This reference point location data is then used to define a transformation vector Vj as discussed above.

When the transformation vector Vj is defined, operation 915 uses the vector Vj to transform the position location information within the electronic model of the upper object into corresponding position locations within a common coordinate system with the physical objects positioned at a desired location. Once the position data transformation operation completes, the process ends 902.

Figure 10:
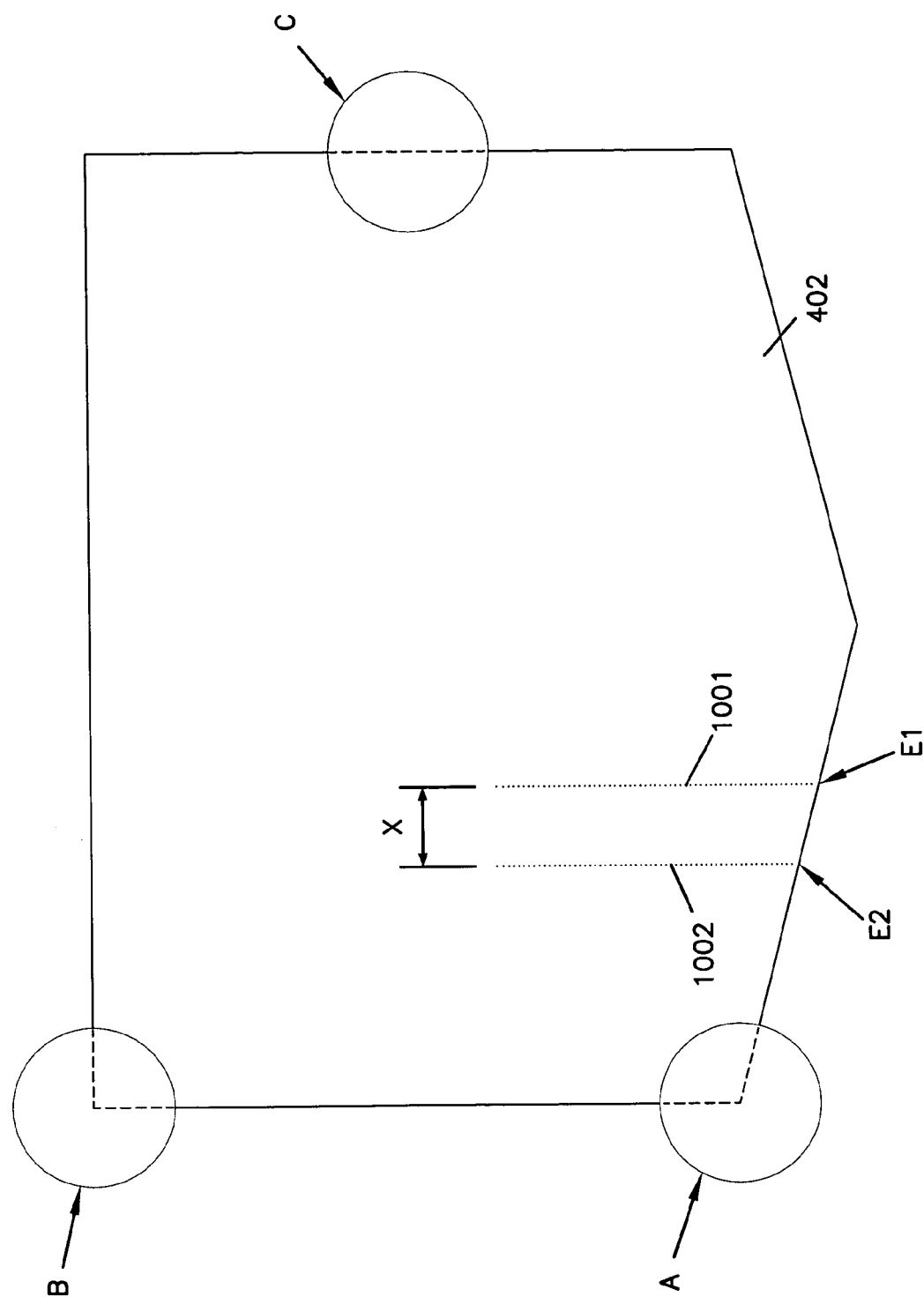
FIG. 10 illustrates a schematic system in which the approximate location of the registration/alignment spheres can be determined by finding two edge points (E1 and E2).

Another feature of the present invention is illustrated in FIG. 10. Here to reduce the scan time and the time necessary to locate the registration/alignment spheres, the system may employ an algorithm to locate two edge points E1 and E2 of the physical model plate module 402. By locating these edge points and recalling the geometry between the edge points, then the first sphere A can be found. The second and third sphere's B and C can then subsequently be found.

More specifically, the scanner first finds the surface of the physical model plate module 402 and then begins scanning along a first scan line designated at 1001. Once the scanner locates the edge point E1, the scanner steps over and performs a second scan along a second scan line designated at 1002. The scan system stores the distance x between the two scan lines 1001 and 1002. Once the second edge point E2 is located, a vector E1E2 is determined and the scanner is able to rapidly move along the vector until it comes to the edge of sphere A. At this time, sphere A is scanned in detail and the location of sphere A is computed. Once vector E1E2 is known and the location of A is known in detail, then spheres B and C can be located more rapidly.

FIG. 3 illustrates an example of a suitable operating environment in which the invention may be implemented. The operation environment is only one example of a suitable operating environment and is not intended to suggest any limitation s to the scope of use or functionality of the invention. Other well known computing systems, environments, and/or configurations that may be suitable for use with the invention include, but are not limited to, personal computers, server computers, held-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired various embodiments.

A processing device attached to a communications network typically includes at least some form of computer readable media. Computer readable media can be any available media that can be accessed by these devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by process devices.

Communication media typically embodies computer readable instructions, data structure, program modules or other data in a modulated data signal such as a carrier wave or other transport mechanism and includes any information delivery media. The term "modulated data signal" means a signal that has one or more of its characteristics set or changed in such a manner as to encode information in a signal. By way of example, and not limitation, communication media includes wired media such as a wired network or direct-wired connection, and wireless media such as an acoustic, RF, infrared and other wireless media. Combinations of any of the above should also be included within the scope of computer readable media.

Additionally, the embodiments described herein are implemented as a logical operation performed by a programmable processing device. The logical operation of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the present invention describe a system, method and article of manufacture for generating an electronic model for a dental impression having a common coordinate system, one skilled in the art will recognize that the use of a particular computing architecture for a data processing system are merely example embodiments of the present invention. It is to be understood that other embodiments may be utilized and operation changes may be made without departing from the scope of the present invention as recited in the attached claims.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method and apparatus for generating an electronic model for a dental impression having a common coordinate system.

I claim:

1. A system for generating an electronic model of a dental study cast, the electronic model having a common coordinate system, the system comprising:
    a base plate module configured to couple to a scanning device;
    a first scanning module configured to couple to the base plate module, the first scanning module being configured to position a first study cast of a first dental arch within the scanning device to generate a first electronic model of the first dental arch, the first scanning module including a first plurality of alignment spheres configured to be scanned by the scanning device;
    a second scanning module configured to position a second study cast of a second dental arch within the scanning device to generate a second electronic model of the second dental arch, the second scanning module including a second plurality of alignment spheres configured to be scanned by the scanning device, the second scanning module being configured to couple selectively to the base plate module and to the first scanning module;
    an articulator configured to couple to the first and second scanning modules to form a combined scanning apparatus, the articulator being configured to position the first scanning module relative to the second scanning module to orient an occlusal surface of the first study cast towards an occlusal surface of the second study cast; and
    a data processing system configured to generate the electronic models corresponding to each of the dental arches within a common coordinate system, the data processing system being configured to obtain position data of at least one of the alignment spheres from the combined scanning apparatus, the data processing system also being configured to transform position data of the first electronic model and the second electronic model based on the position data obtained from the alignment sphere, whereby a composite electronic model in a common coordinate system is generated, the composite electronic model representing the teeth of the upper jaw and the teeth of the lower jaw of the patient.

2. The system according to claim 1, wherein the scanning base plate module comprises an x-axis alignment channel and y-axis alignment channel; and the physical model plate modules comprise the plurality of alignment spheres, the alignment spheres are coupled to the x-axis alignment channel and the y-axis alignment channel to position the second scanning plate module at a known location relative to the base plate module.

3. A method for generating an electronic model of teeth of a patient, the method comprising:
    mounting a first physical model onto a first scanning plate module, the first physical model representing teeth of a lower jaw of a patient, the first scanning plate module positioning the first physical model within a coordinate system of a scanning device, the first scanning plate module including a plurality of alignment spheres and the first scanning plate module coupling the first physical model to a scanning base plate module of the scanning device;
    scanning the first physical model to obtain position data of the teeth of the lower jaw of the patient and position data of the alignment spheres;
    generating a first electronic model representing the teeth of the lower jaw of the patient, the first electronic model including a polygonal mesh representation of the scanned position data of the teeth of the lower jaw;
    mounting a second physical model onto a second scanning plate module, the second physical model representing teeth of an upper jaw of the patient, the second scanning plate module positioning the second physical model within a coordinate system of a scanning device, the second scanning plate module including a plurality of alignment spheres and the second scanning plate module coupling the second physical model to a scanning base plate module of the scanning device;
    scanning the second physical model to obtain position data of the teeth of the upper jaw of the patient and position data of the alignment spheres;
    generating a second electronic model representing the teeth of the upper jaw of the patient, the second electronic model including a polygonal mesh representation of the scanned position data of the teeth of the upper jaw;
    after generating the first and second electronic models, positioning each of the scanning plate modules to arrange the physical models relative to each other based on an interaction between the teeth of the lower jaw and the teeth of the upper jaw to form a composite scanning apparatus;
    scanning one of the alignment spheres within the combined scanning apparatus to obtain position data of the alignment sphere within the combined scanning apparatus; and
    transforming the scanned positional data of the first and second electronic models based at least in part on the position data of the alignment sphere within the combined scanning apparatus to generate a composite electronic model in a common coordinate system, the composite electronic model representing the teeth of the upper jaw and the teeth of the lower jaw of the patient.

4. The method according to claim 3 wherein the method further comprises generating a position transformation vector using positional data obtained by scanning the alignment sphere, the position transformation vector being used to transform the first and second electronic models into a common coordinate system.

5. The method according to claim 3, wherein positioning each of the scanning plate modules comprises positioning the scanning plate modules to arrange the physical models into a first bite position.

6. The method according to claim 5, wherein positioning each of the scanning plate modules comprises positioning the scanning plate modules into an occlusion centric relation position.

* * * * *